United States Patent [19]
Weinberg et al.

[11] Patent Number: 6,014,586
[45] Date of Patent: Jan. 11, 2000

[54] VERTICALLY INTEGRATED SEMICONDUCTOR PACKAGE FOR AN IMPLANTABLE MEDICAL DEVICE

[75] Inventors: Alvin H. Weinberg, Moorpark; Buehl E. Truex, Glendora, both of Calif.

[73] Assignee: Pacesetter, Inc.

[21] Appl. No.: 08/806,364

[22] Filed: Feb. 27, 1997

Related U.S. Application Data

[63] Continuation of application No. 08/560,920, Nov. 20, 1995, abandoned.

[51] Int. Cl.[7] .................................................. A61N 1/372
[52] U.S. Cl. ............................................................. 607/36
[58] Field of Search ........................ 607/36, 37; 257/686, 257/777, 786, 784, 723, 724; 361/735, 760, 783, 813, 820, 777

[56] References Cited

U.S. PATENT DOCUMENTS

| | | |
|---|---|---|
| 3,262,023 | 7/1966 | Boyle . |
| 4,467,400 | 8/1984 | Stopper .................................... 361/777 |
| 4,567,643 | 2/1986 | Droguet et al. . |
| 4,614,194 | 9/1986 | Jones et al. . |
| 4,616,655 | 10/1986 | Weinberg et al. . |
| 4,763,188 | 8/1988 | Johnson . |
| 4,959,749 | 9/1990 | Dzarnoski et al. . |
| 5,012,323 | 4/1991 | Fernworth ............................... 361/813 |
| 5,028,986 | 7/1991 | Sugano et al. . |
| 5,060,027 | 10/1991 | Hart et al. . |
| 5,140,496 | 8/1992 | Heinks et al. . |
| 5,208,782 | 5/1993 | Sakutz et al. ........................... 257/786 |
| 5,291,061 | 3/1994 | Ball . |
| 5,309,020 | 5/1994 | Muresawa et al. . |
| 5,323,060 | 6/1994 | Fogal et al. . |
| 5,330,504 | 7/1994 | Somerville et al. ........................ 607/5 |
| 5,422,435 | 6/1995 | Takier et al. ............................. 257/686 |
| 5,439,482 | 8/1995 | Adams et al. ............................. 607/36 |
| 5,470,345 | 11/1995 | Hassler et al. ............................. 607/36 |
| 5,473,198 | 12/1995 | Hajiyz et al. ............................ 257/786 |

FOREIGN PATENT DOCUMENTS

| | | |
|---|---|---|
| 9215368 | 9/1992 | European Pat. Off. ................. 607/36 |
| 58-92230 | 6/1983 | Japan . |
| 60-182731 | 9/1985 | Japan . |
| 63-128736 | 6/1988 | Japan . |
| 3-169062 | 7/1991 | Japan . |
| 4-56262 | 2/1992 | Japan .................................... 257/686 |
| 5-13663 | 1/1993 | Japan .................................... 257/777 |

OTHER PUBLICATIONS

Tuckerman, D.B., et al., "Laminated Memory: A New 3–Dimensional Packaging Technology for MCMs," *IEEE*, pp. 58–63, (Jul. 1994).

"8 Megabit High Speed CMOS SRAM (DPS512X16MKn3), " *Dense–Pac Microsystems*, pp. 1–8, Revision D, (No date).

*Primary Examiner*—William E. Kamm
*Assistant Examiner*—George R. Evanisko

[57] ABSTRACT

An electronic package having vertically integrated components placed upon a substrate surface is configured to increase packing density of the components. Integrated circuits which are vertically-stacked and attached to the substrate surface communicate with surrounding components through connection to bond pads on the substrate surface. The bond pads can be placed entirely about a perimeter of the integrated circuits to achieve optimal packing density. Individual bond pads may be shared by two or more integrated circuits by connection therewith. In an alternative embodiment, a separate integrated circuit is attached to the substrate adjacent to the stacked integrated circuits with a row of shared bond pads positioned therebetween. Individual passive or active components may be placed between bond pads for incorporation into the circuit structure.

18 Claims, 4 Drawing Sheets

VERTICALLY INTEGRATED SEMICONDUCTOR PACKAGE FOR AN IMPLANTABLE MEDICAL DEVICE

This is a continuation of application Ser. No. 08/560,920 filed on Nov. 20, 1995 now abandoned.

FIELD OF THE INVENTION

This invention relates generally to three-dimensional microelectronic semiconductor circuit structures. More particularly, this invention relates to methods and apparatus for vertically integrating, or stacking, integrated circuit components to minimize the surface mounting area required for such components.

BACKGROUND OF THE INVENTION

For a given electrical apparatus, electronic components such as integrated circuits, and associated analog or logic circuitry, are typically situated and interconnected through conductive pathways situated on, or formed within, a main substrate board. Various configurations of such substrate boards can be used to form circuitry for countless electronic applications.

In implantable devices, such as pacemaker and defibrillator applications, it is important that the size of the main substrate board be as small as possible. One factor requiring a small substrate board is the limited physical dimensions of an associated product which makes use of the board. With such a product of limited dimensions, it becomes crucial not only to use miniature components, but also to configure and package the components in a particular layout so that use of the substrate-board surface area is optimized.

Modern cardiac pacemakers, and other implantable biomedical apparatus, have physical dimensions which are severely restricted. A reduction in pacemaker size translates into a smaller incision in the patient and a lighter pacemaker unit, in general. As implantable biomedical devices increase in complexity, it is a distinct challenge to prevent the size of these devices from increasing as a result.

The electronics in an implantable medical device typically include a microprocessor, Read Only Memory (ROM) or Random Access Memory (RAM) chips, and other associated active and passive components. These components are usually mounted and interconnected onto a microelectronic substrate or printed circuit board. The substrates used in these medical devices are primarily conventional thick film substrates and high temperature cofired ceramic substrates.

The electronics of pacemaker and other implantable medical devices typically contain components interconnected by "chip-and-wire" technology. Chip-and-wire may be defined as hybrid technology employing exclusively face-up-bonded chip devices interconnected to a substrate by "flying" wires, i.e., wirebonds.

Several U.S. patents have disclosed methods to increase the packing density of microelectronic circuit structures. For example, U.S. Pat. No. 3,302,067 issued to Jackson et al. discloses a method of placing circuit modules onto a mounting board. The mounting board is constructed with interconnecting pathways between each of the modules. The modules are constructed with active electronic components on one side and with electrical resistances deposited on an opposite side. The electrical resistances communicate with the active elements by wrap-around conducting pathways which are formed around the edges of the module. While these advances in component packing density are applicable to a number of different devices, many of them are not directly applicable to chip-and-wire technology.

With respect to chip-and-wire devices, several electronic packaging arrangements have been proposed which use multi-stacked integrated circuits connected to surrounding circuitry through bonding wires. For example, in U.S. Pat. No. 5,323,060 issued to Fogal et al., Fogal discloses stacking chips together to create a multi-chip module which is attached to an underlying substrate. The module is electrically connected to the substrate through bonding wires projecting from each individually-stacked chip to various locations on the mounting substrate. In U.S. Pat. No. 5,291,061 issued to Ball, a stacked die device is disclosed wherein pairs of die devices are attached together and their bond pads are alternately connected to a row of lead fingers.

A method of replacing an electronic component attached to a support substrate with bonding wires is shown in U.S. Pat. No. 4,567,643 issued to Droguet et al. In Droguet, a defective component is replaced by stacking an identical component on top of the defective component and then wire-bonding the new component to conducting tracks placed on the substrate. The defective component is then isolated from the conducting tracks by laser cutting away a portion of the track connected to the defective chip.

Along with performance and reliability, one of the ultimate design goals for cardiac pacemaker circuitry is reduced size. This means that a substrate containing the electronic circuitry must have a high component packing density. The mere stacking of integrated circuits by itself, however, is not necessarily an acceptable solution for reducing overall size.

Therefore, there is a need in the art for a vertically integrated semiconductor package for use in an implantable medical device which can significantly increase component packing density.

SUMMARY OF THE INVENTION

The claimed invention incorporates vertical integration packaging techniques for use in devices having limited physical dimensions such as an implantable pacemaker. A further discussion of vertical integration as a means for increasing electronic packing density is set forth in U.S. Pat. No. 4,614,194 and U.S. Pat. No. 4,616,655, which are incorporated by reference as though fully set forth herein.

The apparatus and method disclosed recite a vertically integrated package for an implantable medical device employing chip-and-wire technology. Components of the vertically integrated package are uniquely configured on top of a mounting substrate to achieve optimal packing density.

Major components of the vertically integrated package, such as integrated circuits, contain signal contacts which are commonly connected to a row, or rows, of bonding pads positioned on the surface of the substrate. These major components may be vertically stacked directly on top of one another, i.e., in a "die-on-die" arrangement, or the integrated circuits may be adjacently placed upon the mounting substrate, or both. Contact pads, or signal leads, from two stacked integrated circuits are positioned to define multiple pairs of contact pads. Each pair of contact pads contains a signal contact from each of the stacked integrated circuits. These pairs of contact pads are then connected to a respective one of the bonding pads placed nearby on the substrate.

Conductive traces along the substrate surface are accordingly minimized by connecting individual bond pads to multiple components such as integrated circuits. These "shared" bond pads may be connected to two, three or more components placed adjacent to one another or vertically stacked together.

In a preferred embodiment, a pair of integrated circuit devices are stacked together by an adhesive and placed upon a support substrate. A row of bond pads are formed on the substrate and positioned along an edge of the integrated circuit devices. The integrated circuit devices are uniquely configured allowing connection of individual bond pads within the row to both of the integrated circuit devices, thus minimizing consumed substrate surface area.

Additionally, a third integrated circuit may be placed adjacent to the stacked integrated circuits. The third integrated circuit may be connected to one of the stacked integrated circuits through a separate row of bond pads placed between the first and third integrated circuits. In an alternative embodiment, the third integrated circuit may be interconnected with both of the stacked integrated circuits through a single row of bond pads. Multiple rows of bond pads may be placed around the remaining edges of the stacked integrated circuits, and the third integrated circuit, providing various interconnection possibilities between a single bond pad and multiple integrated circuits.

Active and passive components such as diodes, resistors, capacitors, and the like, are placed appropriately between bond pads, preferably successive bond pads, on the substrate surface. Placement of these components in close proximity to the integrated circuits, and directly attached to the bond pads, further reduces the required substrate surface area to implement a complex circuit structure.

A pacemaker circuit structure designed in accordance with a preferred embodiment optimizes use of substrate surface area by combining vertically-stacked chips with a unique substrate conductive layout. The present invention, therefore, results in high density electronic packages suitable for sophisticated implantable medical devices.

BRIEF DESCRIPTION OF THE DRAWINGS

The above and other aspects, features and advantages of the present invention will be more apparent from the following particular description thereof presented in conjunction with the following drawings wherein.

DETAILED DESCRIPTION OF THE PREFERRED EMBODIMENT

Figure 1:
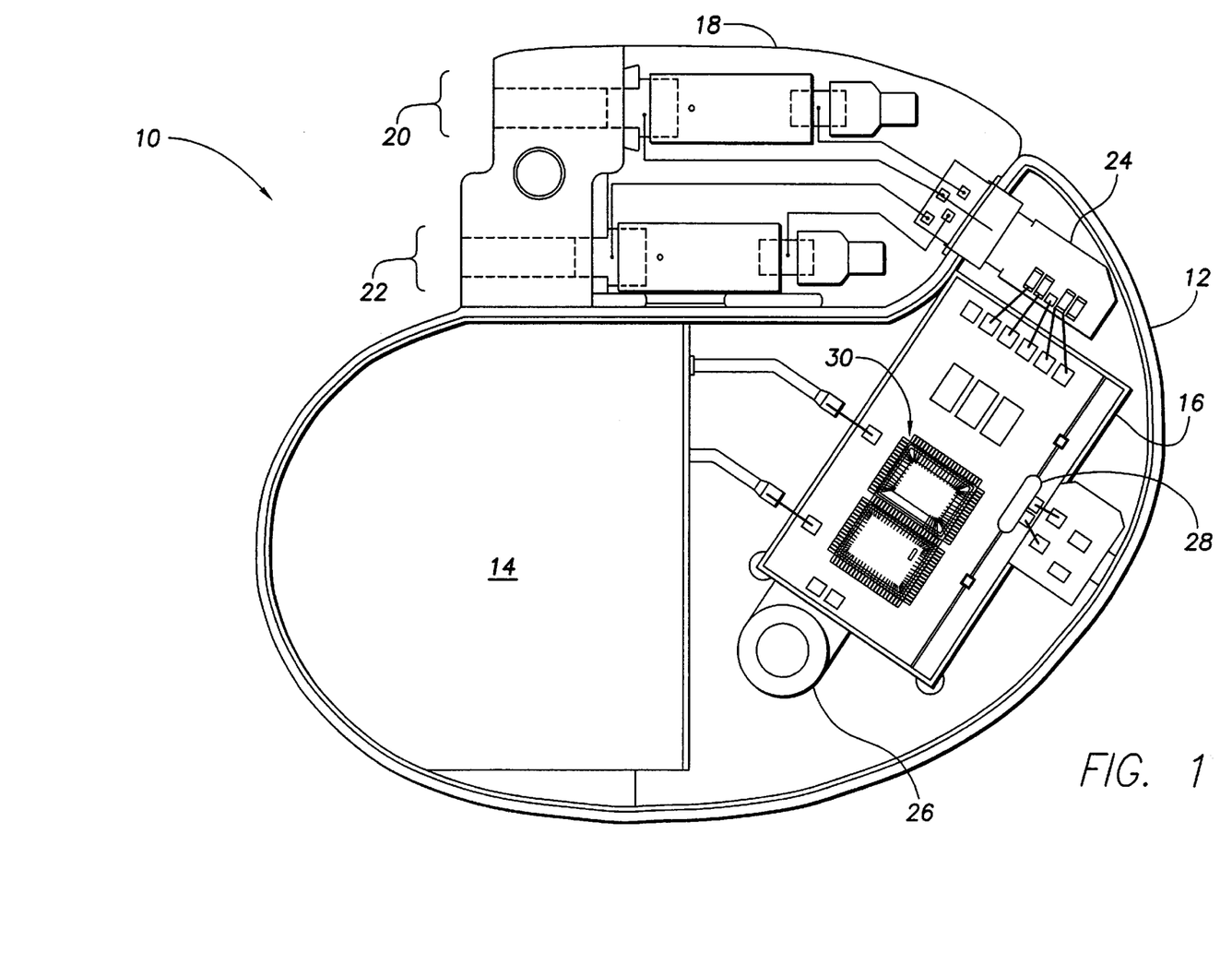
FIG. 1 is a perspective view of an implantable cardiac stimulation device incorporating a preferred embodiment of the invention.

In FIG. 1, an implantable cardiac stimulation device 10 is shown having a housing 12 in which components of the device 10 are placed. Specifically, a typical stimulation device 10 comprises, among other components, a battery 14, an electronic circuitry module 16, a connector top 18, a feedthrough device 24, a telemetry coil 26 and a reed switch 28. The connector top 18 shown in FIG. 1 includes two receptacles 20 and 22 for receiving two implantable stimulation leads (not shown). While the present invention will be described in terms of a dual-chamber stimulation device, it is understood that the present invention could be incorporated into a single-chamber device well. The feedthrough device 24 provides electrical connection between the connector top 18 and the electronic circuitry module 16. The feedthrough device 24 can be of conventional design or may be a multilayered structure as described in copending U.S. Pat. No. 5,620,476, issued Apr. 15, 1997 entitled AN IMPLANTABLE MEDICAL DEVICE HAVING SHIELDED AND FILTERED FEEDTHROUGH ASSEMBLY AND METHODS FOR MAKING SUCH ASSEMBLY, which application is hereby incorporated herein by reference.

In accordance with a preferred embodiment, the electronic circuitry module 16 incorporates a vertically integrated circuit 30. The vertically integrated circuit 30 contains the component circuitry for controlling the generation and delivery of current through the stimulation leads (not shown).

Figure 2:
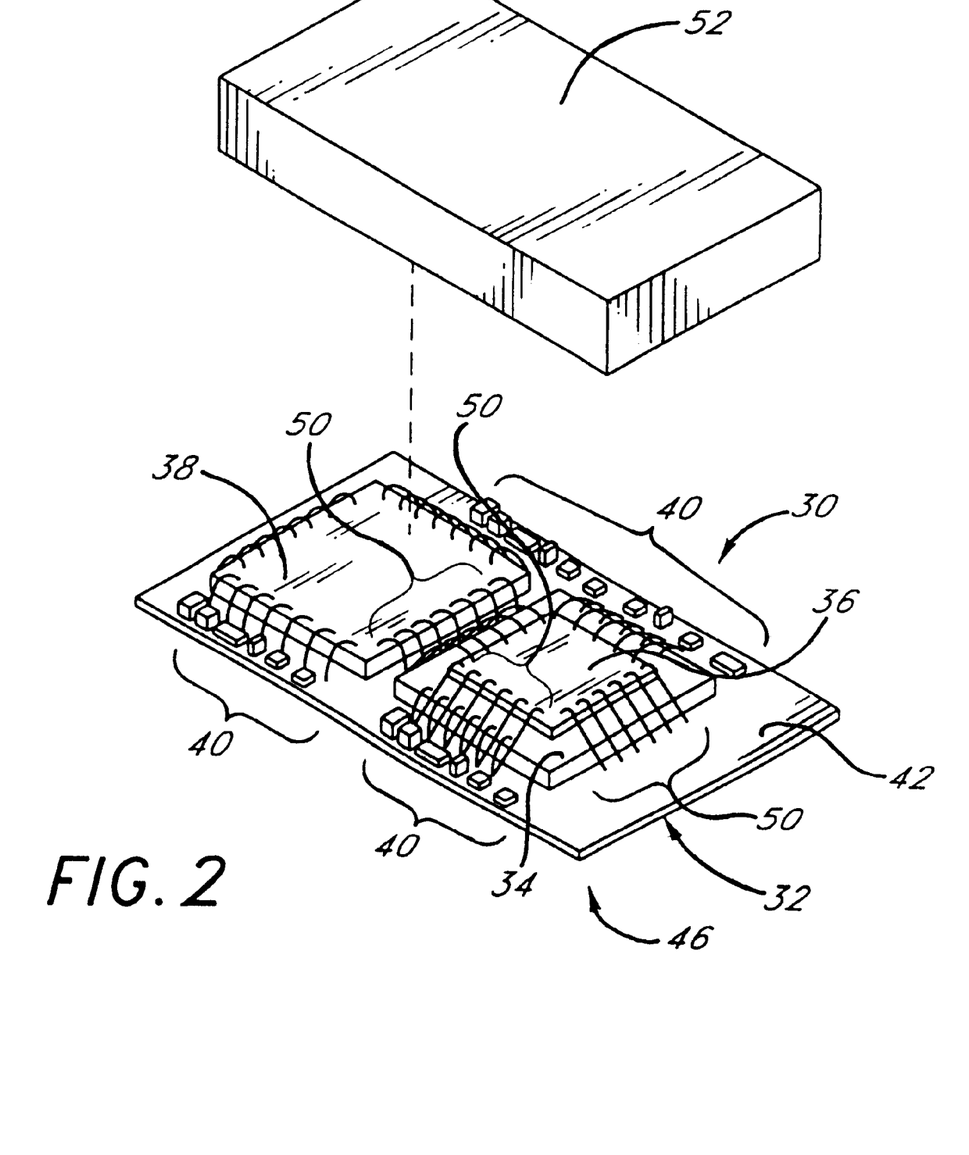
FIG. 2 is a perspective view of a preferred embodiment of a vertically integrated package for use in an implantable medical device.

In FIG. 2, a perspective view of the vertically integrated circuit 30 is shown in association with a package cover 52. The vertically integrated circuit 30 is suitable for use in an implantable medical device such as a cardiac defibrillator, fluid dispensing pump, pacemaker or the like. The vertically integrated circuit 30 includes a main substrate board 32 with a top surface 42 upon which are mounted integrated circuits, or semiconductor "chips", 34, 36, and 38. Additional circuit components 40, which may include active components and passive components, may be mounted around the perimeter of the chips 34 and 38. The integrated circuits 34, 36, and 38, and the components 40 form part of a hybrid circuit structure on the substrate surface 42. All of the components positioned upon the top surface 42 may be mounted using conventional attachment techniques, such as silver epoxy. The substrate 32 is a double-sided planar design wherein a bottom side 46 is capable of supporting large passive components (not shown).

Each of the active devices 34, 36 and 38 is electrically connected, or wire-bonded, to the substrate 32 through multiple wires generally designated 50. The wires 50 are approximately one mil thick and ordinarily made of gold or other suitable material. Connection of the wires 50 is accomplished with conventional methods such as thermosonic bonding. The cover 52 is ultimately placed over the substrate 32 enclosing the underlying circuit components before placement of the vertically integrated circuit 30 in its intended application.

Figure 3:
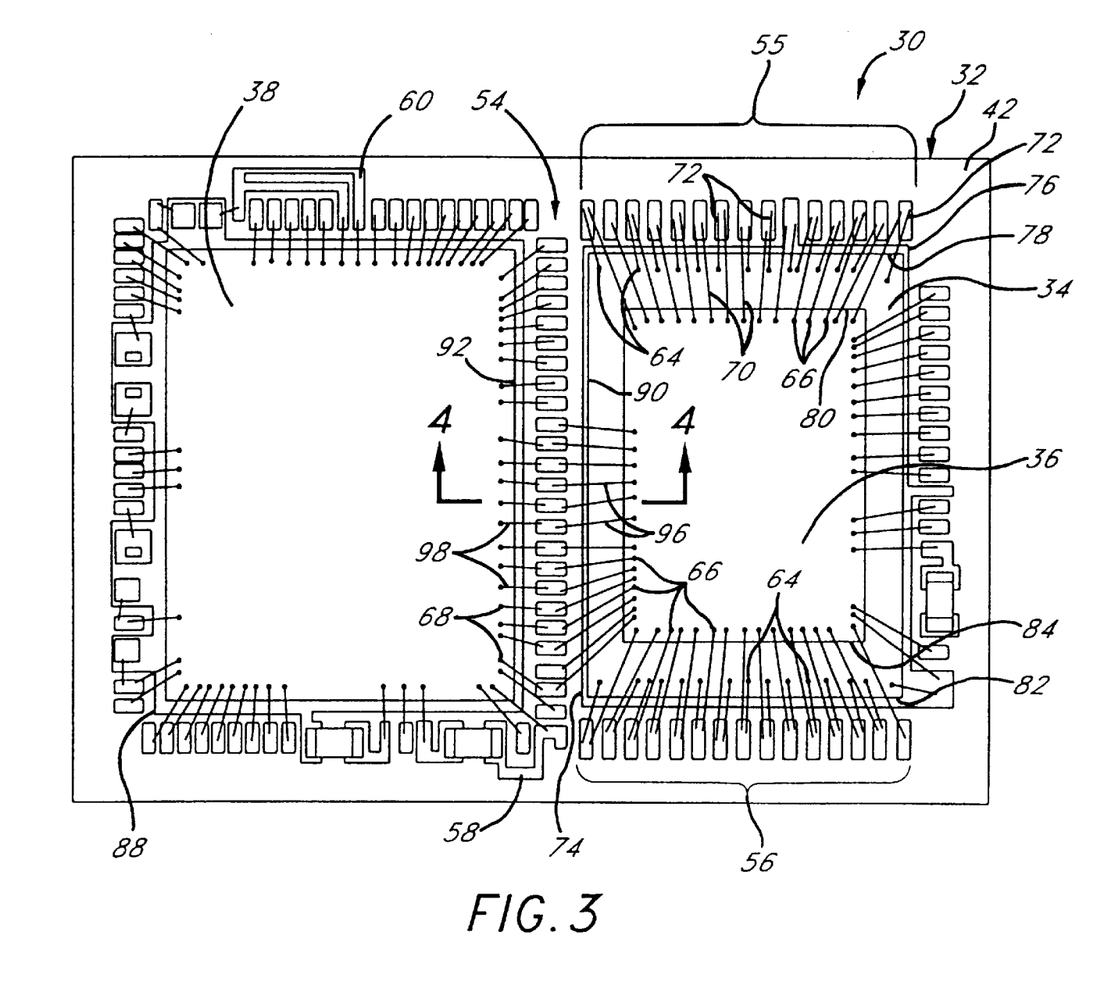
FIG. 3 is a plan view of the vertically integrated package shown in FIG. 2.

FIG. 3 depicts the layout and interconnection of components placed upon the surface 42 of the substrate 32 in accordance with a preferred embodiment. The substrate 32 is a sandwich structure comprised of several layers (not shown) of cofired ceramic. The individual components are interconnected by attachment to conductors placed on the surface 42 of the substrate 32. The conductors include groups of bond pads formed as separate bond pad rows 54, 55 and 56 placed around chips 34 and 38. Additional rows of bond pads as well as various electrically conductive pathways 58 and 60 also surround the chips 34 and 38. Still other conductive pathways (not shown) interconnect individual bond pads placed either on the top surface 42 or the bottom surface 46 (not shown). Such conductive pathways (not shown) are formed between successive layers of the substrate 32 in accordance with conventional methods common to one of ordinary skill in the art.

In conventional printed circuit board layouts, a substantial portion of the substrate surface is occupied by sometimes lengthy conductive pathways which interconnect the circuit components. Use of lengthy conductive pathways on the substrate surface will adversely affect the packing density of components on that surface, as well as increase noise. Accordingly, if the size of the substrate is limited, conventional methods of configuring the circuit layout may prove inadequate. Implantable cardiac stimulation devices are an example of one such application.

As can be seen in FIG. 3, the semiconductor chips 34 and 38 occupy a majority of the surface 42. The chips 34 and 38, along with the vertically-stacked chip 36, are interconnected with the substrate 32 in a manner which minimizes the required size of the substrate 32. Specifically, the integrated circuits 34, 36, and 38 each contain multiple contact pads 64, 66, and 68, respectively. The contact pads 64, 66, and 68 are in turn connected to bond pads placed on the surface 42 of the substrate 32. For example, the row of bond pads 55 are individually connected to the contact pads 64 through bond wires 72. The same individual bond pads are also connected to the contact pads 66 through bond wires 70.

In the preferred embodiment, the chip 34 is placed within a die-attach pad 74 located on the surface 42. An edge 76 of the die-attach pad 74 is aligned parallel to the row of bond pads 55. Edges 78 and 80 of chips 34 and 36, respectively, are also aligned with the edge 76 from within the die-attach pad 74. The contact pads 64 and 66 along the edges 78 and 80 form a set of unique pairs of contact pads wherein each pair comprises a contact pad from the chip 36 and an adjacent contact pad from the underlying chip 34. The pairs of contact pads, while not directly connected together, are in electrical communication through mutual contact, via bond wires 70 and 72, with a corresponding bond pad from the row of bond pads 55.

Similarly, along opposite edges 82 and 84 of chips 34 and 36, respectively, a second set of unique pairs of contact pads are placed for connection to individual bond pads along the row 56. Although not shown, this paired connection scheme could be continued along all four edges of the chip 34. It can be appreciated, however, that not all bond pads along the rows 55 or 56 need be "shared" with contact pads from both of the chips 34 and 36. The exact number of bond pads which are shared will depend upon a specific design. For example, predetermined pin designations of integrated circuits, the size and technical specifications of active and passive components, and the size of the substrate itself all affect the eventual layout chosen for a particular circuit design.

optimally, the layout of the substrate, i.e., the position of all of the components and their interconnecting pathways, will result in a maximum number of bond pads being "shared" by connection to two or more components. Such optimization of the layout can be more easily achieved if the chips 34 and 36 themselves can be engineered for a specific application whereby the contact pads are strategically placed. However, even using standard integrated circuit chips, the packing density of a circuit application can be significantly increased by implementing the concepts of the claimed invention. Such an increase in packing density through use of shared bond pads also significantly reduces noise within the circuit structure.

To further increase packing density, the third integrated circuit 38 is placed on the substrate 32 within a die-attach pad 88 which is adjacent to the vertically-stacked chips 34 and 36. In this configuration, the chips 34 and 38 have commonly-aligned edges 90 and 92, respectively. In between the edges 90 and 92 is the row of bond pads 54 positioned parallel to, i.e., in alignment with, the edges 90 and 92. Individual bond pads from the row of bond pads 54 are selectively connected to either one or both of the chips 34 and 38 through wirebonds 96 and 98, respectively.

Figure 4:
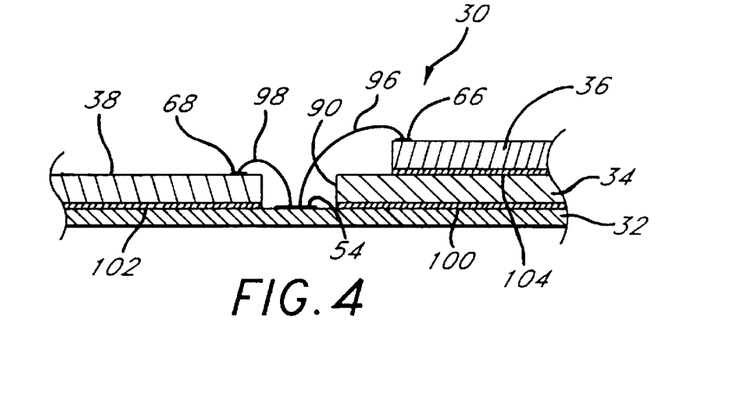
FIG. 4 is an elevation view of the vertically integrated package shown in FIG. 3 taken along the line 4—4.

As shown in FIG. 4, the vertically integrated circuit 30 is depicted as seen along the line 4—4 of FIG. 3. For simplicity, only one wirebond is shown depending from each of the chips 36 and 38 in FIG. 4. The chips 34 and 38 are attached to the substrate 32 by conductive adhesive material 100 and 102, respectively, such as silver epoxy. In a preferred embodiment, the adhesive layers 100 and 102 are first placed on the substrate 32 followed by placement of the chips 34 and 38 thereon.

The chip 36 is attached to the chip 34 by an nonconductive adhesive 104. The adhesive 104, preferably in the nature of a preform, will next be placed on top of the chip 34 followed by placement of the chip 36 thereon.

The adhesive layer 104 may be an epoxy resin or other suitable material which is flexible (low modulus), exhibits low outgassing, is nonconductive and provides adequate bonding adhesion to both silicon and glass. The adhesive material must be highly reliable to withstand temperature cycling, acceleration, and burn-in, as well as meet the requirements of MIL-STD-883 specifications. The adhesive should have a maximum operating temperature greater than or equal to 125° C., and be non-corrosive to die materials such as silicon and glass (chlorine concentrations of less than 1 ppm are preferred).

By selectively connecting individual integrated circuits to shared bond pads, integrated circuits of different functions, may be linked together at common nodes. The particular type of chips used in the vertically integrated circuit 30 of FIG. 4 will vary according to the circuit application. In a preferred embodiment, the vertically integrated techniques described herein are applied to an implantable medical device. In such a device, the integrated circuit 34 is a memory chip, such as a RAM chip, the integrated circuit 36 is a digital chip such as a processor chip, and the integrated circuit 38 is an analog chip. The chip 36 is shown in FIG. 4 to have a smaller dimension than the chip 34 but may extend to the edge 90 of the chip 34. Additionally, the vertical position of the chips 34 and 36 may be transposed if, for instance, the chip 36 were larger than the chip 34.

Figure 5:
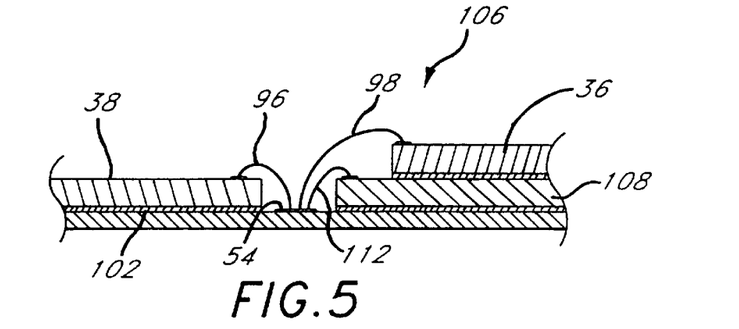
FIG. 5 is an elevation view of an alternative embodiment of a vertically integrated package having bond pads shared by three integrated circuits.

FIG. 5 depicts an alternative embodiment of a vertically integrated semiconductor package 106. In the alternative embodiment, the row of bond pads 54 is shared by three semiconductor chips 36, 38, and a chip 108. The chip 108 has contacts 110 which are connected to individual bond pads from the row 54 by wirebonds 112 (one wirebond shown for simplicity). Use of this configuration will again depend on the specific application of the vertically integrated package.

Figure 6:
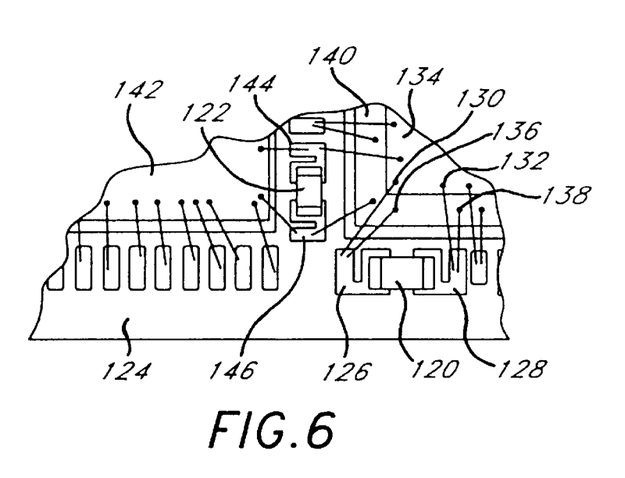
FIG. 6 is a fragmentary, enlarged plan view of an alternative embodiment of a vertically integrated package having individual components placed between successive shared bond pads.

FIG. 6 depicts a partial plan view of a second alternative embodiment whereby additional circuit components 120 and 122 are connected between successive bond pads on a substrate 124. In particular, the circuit component 120 is positioned between, and in electrical communication with, a bond pad 126 and a bond pad 128. A pair of contacts 130 and 136 of chips 134 and 140, respectively, are connected to the bond pad 126. Similarly, a pair of contacts 132 and 138 are connected to the bond pad 128. The circuit component 120 may be any number of various passive or active components such as a resistor, capacitor, diode, transistor or the like. Placement of the component 120 between the bond pads 126 and 128, and aligned with the corresponding row of bond pads, allows such components to be introduced into the surrounding circuit structure without increasing the amount of surface area of the substrate 124. In this manner, the component 120 is electrically connected, via the substrate bond pads 126 and 128, to both of the chips 134 and 140.

In a similar manner, the circuit component 122 is shared by chips 140 and 142 through attachment to common bond pads 144 and 146. It can be appreciated that the components 120 and 122, or similar additional components (not shown), can be placed where needed between successive bond pads.

Through the foregoing description and accompanying drawings, the present invention has been shown to have important advantages over current apparatus and methods for increasing substrate packing density. While the above detailed description has shown, described, and pointed out the fundamental novel features of the invention, it will be understood that various omissions and substitutions and changes in the form and details of the device and process illustrated may be made by those skilled in the art, without departing from the spirit of the invention. Therefore, the invention should be limited in its scope only by the following claims.

What is claimed is:

1. An implantable cardiac stimulation device, comprising:
    electronic circuitry for generating cardiac stimulation pulses in at least one of the absence or presence of certain cardiac events, said electronic circuitry comprising:
        a first integrated circuit chip having a first array of signal contact pads disposed thereon;
        a second integrated circuit chip having a second array of signal contact pads disposed thereon;
        a substrate having a first predefined die-attach area located on a surface of said substrate, said first integrated circuit chip being mounted on said first predefined die-attach area on said surface, said substrate also having a first plurality of bond pads located thereon adjacent said first predefined die-attach area, said second integrated circuit chip being vertically stacked upon said first integrated circuit chip;
        a first plurality of wirebonds, each one of said first plurality of wirebonds extending between a selected one of said first array of signal contact pads to a selected one of said first plurality of bond pads providing electrical communication therebetween;
        a second plurality of wirebonds, each one of said second plurality of wirebonds extending between a selected one of said second array of signal contact pads to a selected one of said first plurality of bond pads providing electrical communication therebetween, wherein at least one of said first plurality of bond pads is commonly shared by one of said first plurality of wirebonds and at least one of said second plurality of wirebonds whereby electrical comminication is enabled between said first and second integrated circuit chips via said shared bond pads in said first plurality of bond pads;
        at least one additional circuit component extending between and electrically connected to two of said bond pads in said first pluralities of bond pads; and
        a housing for hermetically sealing said electronic circuitry therein.

2. The implantable cardiac stimulation device as defined in claim 1, wherein said first and second integrated circuit chips are secured together with a nonconductive bonding material.

3. The implantable cardiac stimulation device as defined in claim 2, wherein said nonconductive bonding material comprises a preformed adhesive segment placed between said first and second integrated circuit chips.

4. The implantable cardiac stimulation device as defined in claim 2, wherein nonconductive bonding material comprises a nonconductive epoxy resin.

5. The implantable cardiac stimulation device as defined in claim 1, wherein said first array of signal contact pads on said first integrated circuit chip is in approximate alignment with said second array of signal contact pads on said second integrated circuit chip.

6. The implantable cardiac stimulation device as defined in claim 1, wherein said at least one additional circuit component comprises a circuit component selected from the group consisting of active circuit components and passive circuit components.

7. The implantable cardiac stimulation device as defined in claim 1, wherein said at least one additional circuit component comprises a circuit component selected from the group consisting of diodes, resistors, and capacitors.

8. The implantable cardiac stimulation device as defined in claim 1, wherein said substrate has a second predefined die-attach area located on said surface of said substrate adjacent to said first predefined die-attach area, said electronic circuitry further comprising:
    a third integrated circuit chip mounted on said second predefined die-attach area on said substrate adjacent to said vertically-stacked first and second integrated circuit chips, said third integrated circuit chip having a third array of signal contact pads disposed thereon, said substrate also having a second plurality of bond pads located thereon adjacent said second die-attach area, wherein the ones of said first and second pluralities of bond pads which are located between said first and second die-attach areas define a single row of bond pads common to said first and second pluralities of bond pads;
    a third plurality of wirebonds, each one of said third plurality of wirebonds extending between a selected one of said signal contact pads on said third array of signal contact pads to a selected one of said bond pads on said common row of bond pads providing electrical connection therebetween;
    fourth plurality of wirebonds, each one of said fourth plurality of wirebonds extending between a selected one of said signal contact pads on one of said first or second arrays of signal contact pads to a selected one of said bond pads on said common row of bond pads, wherein at least one of said bond pads in said common row is commonly shared by one of said third plurality of wirebonds and at least one of said fourth plurality of wirebonds whereby electrical communication is enabled between said third integrated circuit chip and at least one of said first and second integrated circuit chips via said shared bond pads in said common row of bond pads.

9. The implantable cardiac stimulation device as defined in claim 8, wherein a first one of said first, second, and third integrated circuit chips comprises a memory chip, a second one of said first, second, and third integrated circuit chips comprises a digital logic chip, and a third one of said first, second, and third integrated circuit chips comprises an analog chip.

10. The implantable cardiac stimulation device as defined in claim 9, wherein said memory chip has a control program stored therein, and wherein said analog chip includes sense amplifier circuitry and pulse generating circuitry therein, said analog chip being controlled by said digital logic chip based on said stored control program in said memory chip; and wherein said sense amplifier and pulse generator circuitry of said analog chip electrically communicate to said digital logic chip via third and fourth wirebonds.

11. The implantable cardiac stimulation device as defined in claim 9, wherein said first integrated circuit chip comprises said memory chip, said second integrated circuit chip comprises said digital logic chip, and said third integrated circuit chip comprises said analog chip.

12. The implantable cardiac stimulation device as defined in claim 8, wherein said electronic circuitry comprises sensing circuitry for sensing cardiac events and pulse generating circuitry for generating cardiac stimulation pulses, and wherein a first one of said first, second, and third integrated circuit chips comprises a memory chip having a control program stored therein, a second one of said first, second, and third integrated circuit chips comprises a processor chip for controlling the operation of said implantable cardiac stimulation device based on said stored control program, and a third one of said first, second, and third integrated circuit chips comprises a chip having said sense amplifier circuitry and said pulse generating circuitry incorporated therein, wherein said first, second and third integrated circuit chips electrically communicate via said first, second, third and fourth wirebonds.

13. The implantable cardiac stimulation device as defined in claim 1, further comprising:
    a third integrated circuit chip vertically stacked upon said second integrated circuit chip, said third integrated circuit chip having a third array of signal contact pads disposed thereon; and
    a third plurality of wirebonds, each one of said third plurality of wirebonds extending between a selected one of said third array of signal contact pads to a selected one of said first plurality of bond pads.

14. The implantable cardiac stimulation device as defined in claim 13, wherein said first array of signal contact pads on said first integrated circuit chip is in approximate alignment with said second array of signal contact pads on said second integrated circuit chip, and wherein said third array of signal contact pads on said third integrated circuit chip is in approximate alignment with one of said first and second arrays of signal contact pads.

15. An implantable cardiac stimulation device, comprising:
    electronic circuitry for generating cardiac stimulation pulses in at least one of the absence or presence of certain cardiac events, said electronic circuitry comprising:
        a first integrated circuit chip having a first array of signal contact pads disposed thereon;
        a second integrated circuit chip having a second array of signal contact pads disposed thereon;
        a third integrated circuit chip having a third array of signal contact pads disposed thereon;
        a substrate having adjacent first and second predefined die-attach areas located on a surface of said substrate, said substrate also having a first plurality of bond pads located thereon adjacent said first predefined die-attach area and a second plurality of bond pads located thereon adjacent said second predefined die-attach area, said first and second pluralities of bond pads together comprising a single row of bond pads located between said first and second predefined die-attach areas and common to said first and second pluralities of bond pads, said first integrated circuit chip being mounted on said first predefined die-attach area on said surface of said substrate, said second integrated circuit chip being vertically stacked upon said first integrated circuit, chip and said third integrated circuit chip being mounted on said second predefined die-attach area on said surface of said substrate;
        a first plurality of wirebonds, each one of said first plurality of wirebonds extending between a selected one of said signal contact pads on said first array of signal contact pads to a selected one of said bond pads on said common row of bond pads providing electrical connection therebetween;
        a second plurality of wirebonds, each one of said second plurality of wirebonds extending between a selected one of said signal contact pads on said second array of signal contact pads to a selected one of said bond pads on said common row of bond pads providing electrical connection therebetween;
        a third plurality of wirebonds, each one of said third plurality of wirebonds extending between a selected one of said signal contact pads on said third array of signal contact pads to a selected one of said bond pads on said common row of bond pads providing electrical connection therebetween, wherein at least one of said bond pads on said common row of bond pads is commonly shared by at least two wirebonds from said first, second and third pluralities of wirebonds whereby electrical communication is enabled between at least two of said first, second and third integrated circuit chips via said shared bond pads;
        at least one additional circuit component extending between and electrically connected to two of said bond pads on said first and second pluralities of bond pads; and
        a housing for hermetically sealing said electronic circuitry therein.

16. An implantable cardiac stimulation device, comprising:
    electronic circuitry for generating cardiac stimulation pulses in at least one of the absence or presence of certain cardiac events, said electronic circuitry comprising:
        a substrate having adjacent first and second predefined die-attach areas located on a surface of said substrate, said substrate having a row of bond pads located on the substrate and positioned between said first and second die-attach pads;
        a first integrated circuit chip having a first array of signal contact pads disposed thereon, said first integrated circuit chip being mounted on said first predefined die-attach area on said surface of said substrate;
        a first plurality of wirebonds, each one of said first plurality of wirebonds extending between a selected one of said signal contact pads on said first array of signal contact pads to a selected one of said bond pads on said row of bond pads providing electrical connection therebetween;
        a second integrated circuit chip having a second array of signal contact pads disposed thereon, said second integrated circuit chip being vertically stacked upon said first integrated circuit chip;
        a second plurality of wirebonds, each one of said second plurality of wirebonds extending between a selected one of said signal contact pads on said second array of signal contact pads to a selected one of said bond pads on said row of bond pads providing electrical connection therebetween, wherein at least one of said bond pads is commonly shared by one of said first plurality of wirebonds and at least one of said second plurality of wirebonds whereby electrical communication is enabled between said first and second integrated circuit chips via said shared bond pads;

a third integrated circuit chip having a third array of signal contact pads disposed thereon, said third integrated circuit chip being mounted on said second predefined die-attach area on said surface of said substrate;

a third plurality of wirebonds, each one of said third plurality of wirebonds extending between a selected one of said signal contact pads on said third array of signal contact pads to a selected one of said bond pads on said row of bond pads providing electrical communication therebetween;

a fourth plurality of wirebonds, each one of said third plurality of wirebonds extending between a selected one of said signal contact pads on one of said first or second arrays of signal contact pads to a selected one of said bond pads on said row of bond pads providing electrical communication therebetween and enabling electrical communication to between said third integrated circuit chip and at least one of said first and second integrated circuit chips;

at least one additional circuit component extending between and electrically connected between two of said first or second bond pads located on said substrate; and a housing for hermetically sealing said electronic circuitry therein.

17. An implantable cardiac stimulation device, comprising:

electronic circuitry for generating cardiac stimulation pulses in at least one of the absence or presence of certain cardiac events, said electronic circuitry comprising:

a first integrated circuit chip having a first array of signal contact pads disposed thereon;

a second integrated circuit chip having a second array of signal contact pads disposed thereon;

a substrate having adjacent first and second predefined die-attach areas located on a surface of said substrate, said substrate also having a first plurality of bond pads located thereon adjacent said first predefined die-attach area and a second plurality of bond pads located thereon adjacent said second predefined die-attach area, said first and second pluralities of bond pads together comprising a single row of bond pads located between said first and second predefined die-attach areas and common to said first and second pluralities of bond pads, said first integrated circuit chip being mounted on said first predefined die-attach area on said surface of said substrate, and said second integrated circuit chip being mounted on said second predefined die-attach area on said surface of said substrate;

a first plurality of wirebonds, each one of said first plurality of wirebonds extending between a selected one of said first arrays of signal contact pads to a selected one of said first plurality of bond pads providing electrical communication therebetween;

a second plurality of wirebonds, each one of said second plurality of wirebonds extending between a selected one of said signal contact pads on said second array of signal contact pads to a selected one of said second plurality of bond pads providing electrical communication therebetween, wherein at least one of said bond pads is common to said first and second pluralities of bond pads and is commonly shared by one of said first plurality of wirebonds and at least one of said second plurality of wirebonds whereby electrical communication is enabled between said first and said integrated circuit chips via said shared bond pads;

at least one additional circuit component extending between and electrically connected to two of said bond pads on said first and second plurality of bond pads; and a housing for hermetically sealing said electronic circuitry therein.

18. An implantable cardiac stimulation device, comprising:

electronic circuitry for generating cardiac stimulation pulses in at least one of the absence or presence of certain cardiac events, said electronic circuitry comprising:

a first integrated circuit chip having a first array of signal contact pads disposed thereon;

a second integrated circuit chip having a second array of signal contact pads disposed thereon;

a substrate having a first predefined die-attach area located on a surface of said substrate, said first integrated circuit chip being mounted on said first predefined die-attach area on said surface, said substrate also having a plurality of bond pads located thereon adjacent said first predefined die-attach area, said second integrated circuit chip being vertically stacked upon said first integrated circuit chip;

a first plurality of wirebonds, each one of said first plurality of wirebonds extending between a selected one of said signal contact pads on said first array of signal contact pads to a selected one of said bond pads on said first plurality of bond pads providing electrical communication therebetween;

second plurality of wirebonds, each one of said second plurality of wirebonds extending between a selected one of said signal contact pads on said second array of signal contact pads to a selected one of said bond pads providing electrical communication therebetween, wherein at least one of said bond pads is commonly shared by one of said first plurality of wirebonds and at least one of said second plurality of wirebonds whereby electrical communication is enabled between said first and second integrated circuit chips via said shared bond pads; and at least one additional circuit component extending between and electrically connected to two of said bond pads.

* * * * *